United States Patent
Plog et al.

[11] Patent Number: 5,965,451
[45] Date of Patent: Oct. 12, 1999

[54] USE OF A GAS SENSOR FOR THE SELECTIVE DETECTION OF HYDROCARBONS IN LOW-OXYGEN GASES

[75] Inventors: Carsten Plog; Werner Maunz, both of Markdorf, Germany

[73] Assignee: Dornier GmbH LHG, Friedrichshafen, Germany

[21] Appl. No.: 08/901,064

[22] Filed: Jul. 28, 1997

[30] Foreign Application Priority Data

Jul. 26, 1996 [DE] Germany ............... 196 30 209

[51] Int. Cl.⁶ .......... G01N 27/02; G01N 33/22; G01N 27/22
[52] U.S. Cl. ............... 436/139; 422/90; 422/98; 436/140; 436/141; 436/142; 436/143; 436/149; 436/151; 436/152; 436/159; 436/160
[58] Field of Search .......... 422/90, 98; 502/74; 436/139–143, 149, 151, 152, 155, 159, 160

[56] References Cited

U.S. PATENT DOCUMENTS

| | | |
|---|---|---|
| 4,453,151 | 6/1984 | Leary et al. ............ 422/90 X |
| 4,980,326 | 12/1990 | Hinnenkamp ............ 502/74 X |
| 5,143,696 | 9/1992 | Haas et al. ............ 422/90 |
| 5,296,196 | 3/1994 | Takeshima . |
| 5,357,749 | 10/1994 | Ohsuga et al. . |

FOREIGN PATENT DOCUMENTS 0 426 989 A1 1/1990 European Pat. Off. .

OTHER PUBLICATIONS

K. Alberti et al, *Catal. Today* 1991, 8, 509–513.
K. Alberti et al, *Chem.–Ing.–Tech.* 1993, 65, 940–943.
K. Alberti et al, *Sens, Actuators* 1994, 21 B, 39–50.
C. Plog et al, *Sens, Actuators* 1995, B25, 403–406.
P. Kurzweil et al, *Sens, Actuators* 1995, B25, 653–656.

*Primary Examiner*—Arlen Soderquist
*Attorney, Agent, or Firm*—Evenson, McKeown Edwards & Lenahan P.L.L.C.

[57] ABSTRACT

The invention provides a gas sensor for selective detection of hydrocarbons in low-oxygen gases, having a capacitive element and a gas-permeable sensitive layer as a dielectric. The sensitive layer is a precious-metal-doped zeolite which has a regular crystalline structure made of primary pores whose diameter is in the order of the gas-kinetic diameter of the gas molecules to be detected.

12 Claims, 4 Drawing Sheets

USE OF A GAS SENSOR FOR THE SELECTIVE DETECTION OF HYDROCARBONS IN LOW-OXYGEN GASES

BACKGROUND AND SUMMARY OF THE INVENTION

This application claims the priority of German Application No. 196 30 209.9-52, filed Jul. 26, 1996, the disclosure of which is expressly incorporated by reference herein.

The invention relates to the use of a gas sensor for the selective detection of hydrocarbons (in the following also abbreviated HC) in low-oxygen gases.

It is known to use hydrocarbon sensors to determine the efficiency of exhaust gas after treatment systems on motor vehicles having Otto internal-combustion engines. A special requirement with respect to the hydrocarbon sensor is its insensitivity to CO and $H_2$, since both such constituents are present in large quantities—compared with hydrocarbons—in the exhaust gas of Otto engines.

European Patent Document EP 0 426 989 B1 discloses a selective chemical sensor for gases which meets these requirements. In one embodiment, the sensor consists of a platinum-containing zeolitic layer on an interdigitated capacitor structure. (In the following, "interdigitated capacitor" is sometimes abbreviated IDC). In "Sensors and Actuators", B 24-25 (1995) 403–406, it is shown that a PTNaY-IDC sensor produced on this basis by means of screen printing at 350° on air has 1,000 ppm butane while, at the same time, neither 1,000 ppm CO, nor 1,000 ppm $H_2$ are detected.

Another difficult requirement when using Otto internal-combustion engine is the considerably reduced oxygen concentration (in the range of $\lambda=1$) in comparison to atmospheric conditions. Simultaneously, hydrocarbons in concentrations of significantly below 100 ppm must be detected.

The sensors described in the two above-mentioned documents relate to the detection of hydrocarbons exclusively in high-oxygen gases, for example, in ambient air (oxygen proportion approximately 20%). In the case of a high oxygen concentration, the hydrocarbons and the CO and the hydrogen in the course of a catalytic total oxidation are in each case completely converted into the thermodynamically most stable compounds. In the case of hydrocarbons, $CO_2$ and $H_2O$ are produced; in the case of CO, only $CO_2$ is produced; and, in the case of $H_2$, only $H_2O$ is produced. The catalytic activity of the precious-metal-containing zeolites considered here is so high that $H_2$ is completely converted even at room temperature; and CO is completely converted at a temperature below 100° C. In contrast, a significantly higher temperature is required for the catalytic conversion of hydrocarbons. At the operating temperature of the hydrocarbon sensor, the reaction duration for the total conversion of hydrocarbons is significantly greater than that of $H_2$ and CO.

At a given temperature, cations jump to adjacent adsorptive states in zeolite's pore system under the force of an electric field so that a mobility of cations in the zeolite pore system is established. In case of an alternating voltage and given cation mass, mobility depends on frequency. Thus, the zeolite sensor system will respond with frequency dependent impedance when alternating voltage is applied. The cation mobility may be influenced, if a chemical reaction takes place within the extremely narrow pore systems of zeolites. Whether or not a measurable sensor effect occurs depends qualitatively on whether or not the duration of catalytic reaction and cation jump velocity will fit together.

The duration of the catalytic reaction, the ionic conductibility of the zeolite at the operating temperature of the sensor, the steric conditions of the pore system of the zeolites (that is, the spacing of the cationic adsorption sites and of the catalytically effective centers) must be precisely coordinated with one another. In the case of catalytical total oxidation of hydrocarbons the mobility decreases which leads to the sensor effect in EP 0 426 989 B1. But in the case of catalytic total oxidation of hydrogen and CO at comparable temperatures no sensor effect occurs, as the duration of catalytic reaction and cation jump velocity don't fit.

In the case of very low oxygen concentrations, the hydrocarbons are only partially oxidized instead of totally oxidized as described above, and different reaction times and reaction products will occur. For such catalytical partial oxidation of hydrocarbons which is the subject of the present patent it is unknown whether or not duration of catalytic reaction and cation jump velocity will fit together. No person skilled in the art therefore could say in advance whether a sensor effect will occur with this type of sensor in the case of catalytical partial oxidation of hydrocarbons. That is, the essential principle which the function of the sensor according to the EP 0 426 989 B1 is based on is a total oxidation. Consequently a person skilled in the art should expect, that this sensor doesn't work when a gas containing a low concentration of oxygen is used. Thus, the above-mentioned known hydrocarbon sensors do not appear to be suitable for detecting hydrocarbons with very low oxygen contents, such as occur in the exhaust case of Otto internal-combustion engines wherein $\lambda=1$.

One object of the invention is to provide a sensor for the selective detection of hydrocarbons in low-oxygen gases ($O_2$-proportion lower than 10,000 ppm).

This and other objects and advantages are achieved by the hydrocarbon detector according to the invention. Surprisingly, it was found that the hydrocarbon-sensitive sensor, which is known per se from European Patent Document EP 0 426 989 B1, also has a high sensitivity in the case of a reduced oxygen content. The sensor according to the invention therefore comprises:

a component operating as a capacitor, a gas-permeable sensitive layer as a dielectric, the sensitive layer being a precious-metal-doped zeolite which has a regular crystalline structure made of primary pores whose diameter is on the order of the gas-kinetic diameter of the gas molecules to be detected.

The sensor is based on the following measuring principle: The impedance of the sensor is (as noted previously) a function of both the applied frequency and the ionic conductibility of the zeolite, the latter being influenced by the interaction of the measuring gas component with the interior zeolite surface. The catalytic conversion of the hydrocarbons on the precious-metal centers in the pores of the zeolites, at the sensor operating temperature, does not occur infinitely fast, but at a finite speed. During the time period of the catalytic conversion, the mobility of the cations in the electric field is hindered by the reaction which results in an increase of the resistance in the considered frequency range. The operating temperature of the sensor is in the range between 300° C. and 500° C.

Detection is achieved by determining the impedance of the sensor at a suitable fixed frequency.

In a preferred embodiment, a ZSM5-zeolite is used as the zeolite, particularly having a module $SiO_2/Al_2O_3$ (that is, a ratio of the content of $SiO_2$ and $Al_2O_3$ to zeolite) of 20 to 50. Pt or Pd, particularly at a proportion of from 0.1 to 5% by weight are preferably used as zeolite crystallites. A ZSM5-zeolite with a Pt fraction of 3% by weight in the zeolite powder was found to be particularly advantageous.

The following table lists several zeolites according to the invention together with their respective pore diameter:

| | |
|---|---|
| ZSM5 | 0.53 nm * 0.56 nm |
| mordenite | 0.67 nm * 0.70 nm |
| beta | 0.76 nm * 0.64 nm |
| Y | 0.74 nm |

Other objects, advantages and novel features of the present invention will become apparent from the following detailed description of the invention when considered in conjunction with the accompanying drawings.

DETAILED DESCRIPTION OF THE DRAWINGS

Figure 1:
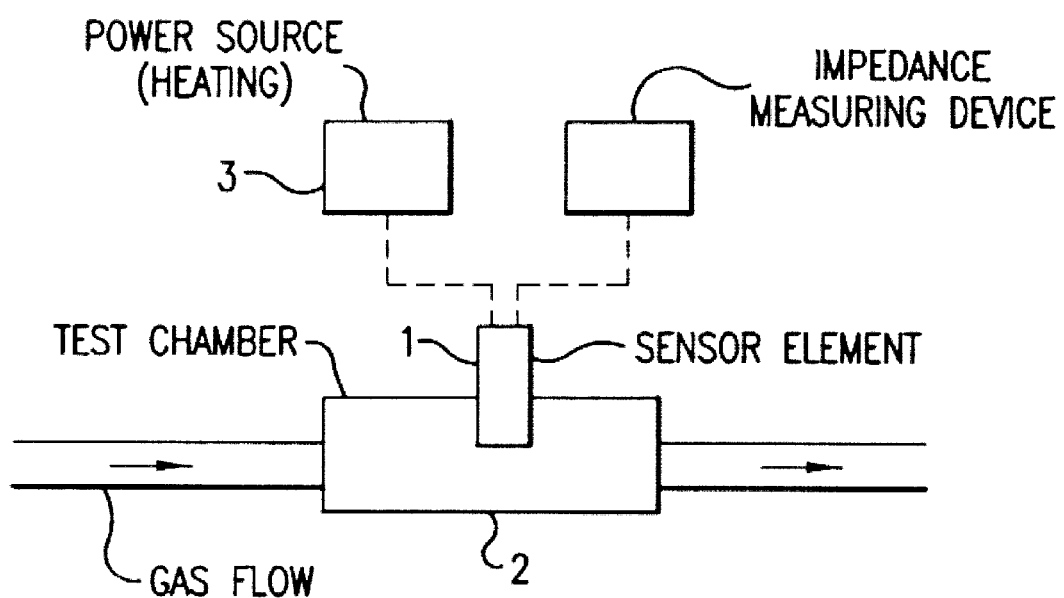
FIG. 1 is a schematic depiction of a sensor according to the invention disposed in an exhaust gas system.

FIG. 1 shows a gas sensor for the selective detection hydrocarbons according to the invention arranged in an exhaust gas system of, for example, a motor vehicle. The sensor element 1 is arranged in a chamber 2, through which exhaust gas flows. A power source 3 supplies energy to the sensor element 1, while an impedance measuring device 5 is provided to measure the impedance of the sensor element 1 at a fixed frequency, for detection of hydrocarbons.

Figure 2A:
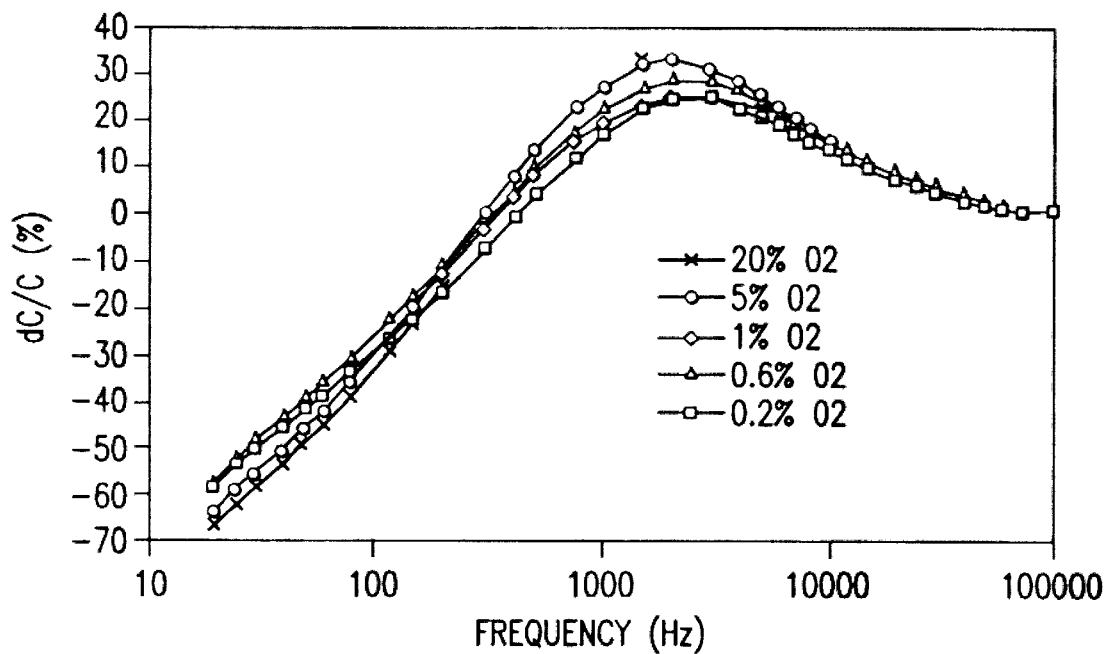
FIGS. 2a and 2b are diagrams which show the influence of oxygen on the sensitivity (relative capacitance change $\Delta C/C$ and relative resistance change $\Delta R/R$) of the sensor according to the invention in the case of a hydrocarbon admission of 1,000 ppm of butane, with 5% $H_2O$, and a remainder of $N_2$, as a function of the frequency.
Figure 2B:
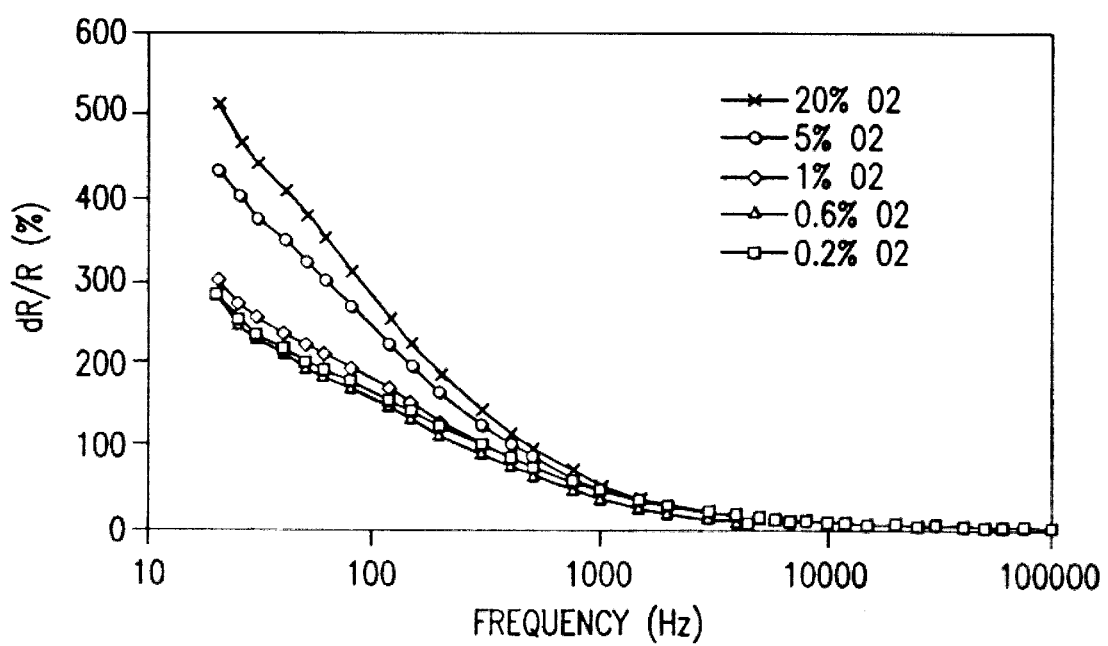

FIG. 2a shows the effect of a decrease of the oxygen concentration on the relative capacitance changes $\Delta C/C$ while FIG. 2b shows the relative resistance change $\Delta R/R$ obtained from the impedance measurement as a function of the frequency, when 1,000 ppm butane are added as the hydrocarbon to be detected. The applied frequencies are in each case entered on the abscissa. The value $\Delta C/C$ and $\Delta R/R$ is entered on the ordinate as a percent. In this case, C and R are calculated from the imaginary and real components of the measured complex impedance in the case of a fixed frequency. $\Delta C$ and $\Delta r$ indicate the difference of the C-value and R-values respectively which were determined with and without the butane admission at the same frequency. Five series of measurements are shown, in each of which the $O_2$-content is held constant, but was reduced from 20% to 0.2%, from one series of measurements to the next.

As demonstrated in FIG. 2a, the oxygen reduction causes a change of capacitance, which is almost unnoticeable over the whole frequency range. Thus, particularly at a low frequency, the capacitance reduction of approximately –60% is sufficiently high.

Although the resistance change (FIG. 2.b,) decreases with a reduction of the oxygen content, even at 0.2% oxygen, a sufficiently high sensitivity still remains. The influence of oxygen in the range of low concentrations of 0.2, 0.6 and 1.0% (and thus within the usage range in the case of the Otto engine) is very low.

Figure 3:
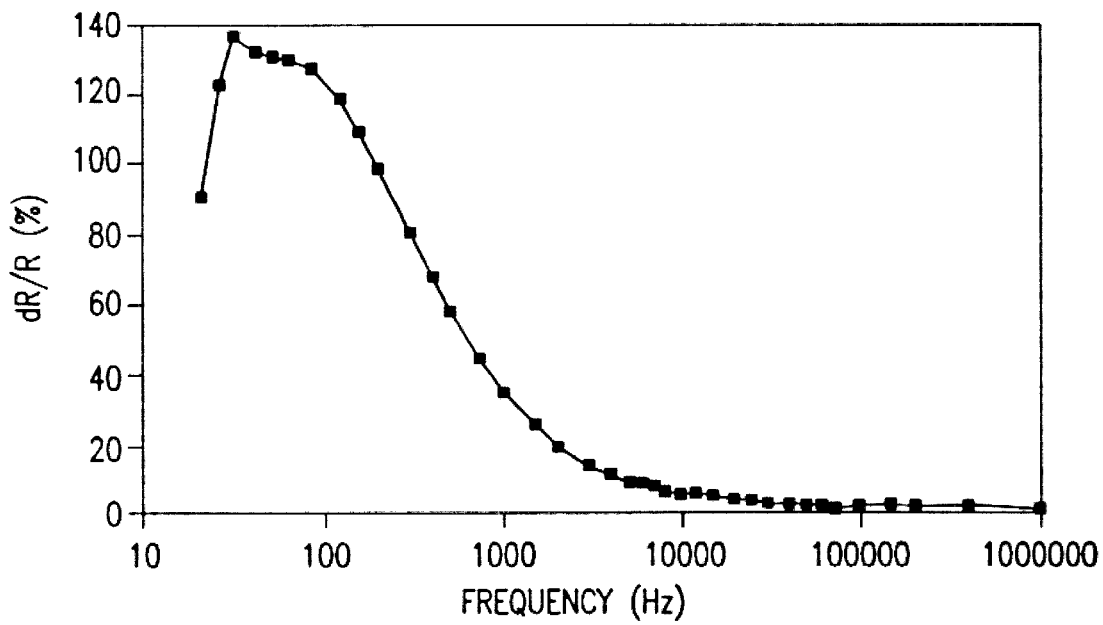
FIG. 3 is a diagram of the relative resistance change $\Delta R/R$ of a sensor according to the invention in the case of a hydrocarbon admission of 500 ppm of a propane/propene mixture with 0.6% $O_2$, 5% $H_2O$, and a remainder of $N_2$, as a function of the frequency.
Figure 4:
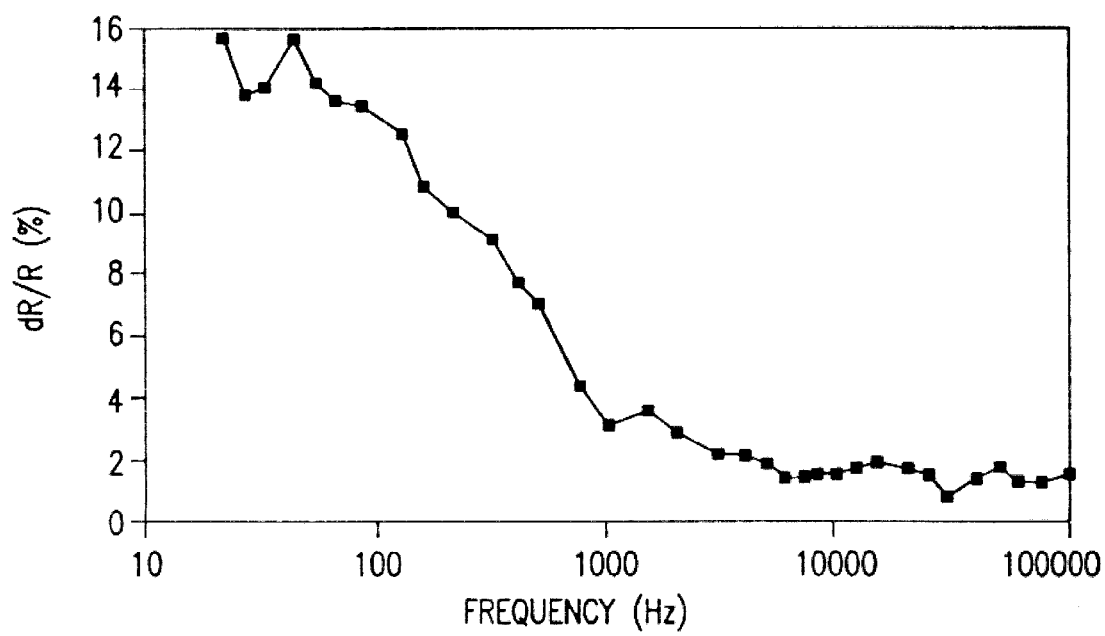
FIG. 4 is a diagram of the relative resistance change $\Delta R/R$ of a sensor according to the invention in the case of a hydrocarbon admission with 20 ppm of an ethane/ethylene/ethyne/propene mixture with 0.6% $O_2$, 5% $H_2O$, and the remainder $N_2$, as a function of the frequency.

FIGS. 3 and 4 each depict the values $\Delta R/R$ obtained from the impedance measurement as a function of the frequency. FIG. 3 shows that 500 ppm of a propane/propene mixture can be detected with a sufficient sensitivity at 0.6% $O_2$. The same applies to the detection of 20 ppm of an ethane/ethylene/ethyne/propene mixture at 0.6% $O_2$, as shown in FIG. 4.

Figure 5A:
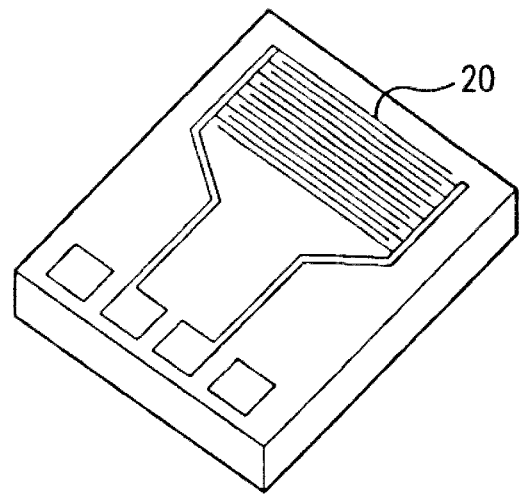
FIGS. 5a–c illustrate the sensor according to the invention constructed as an interdigitated capacitor structure, with a zeolite layer mounted on it as the dielectric.
Figure 5B:
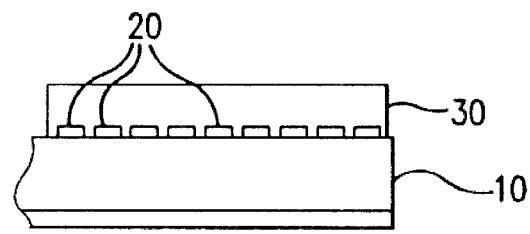
Figure 5C:
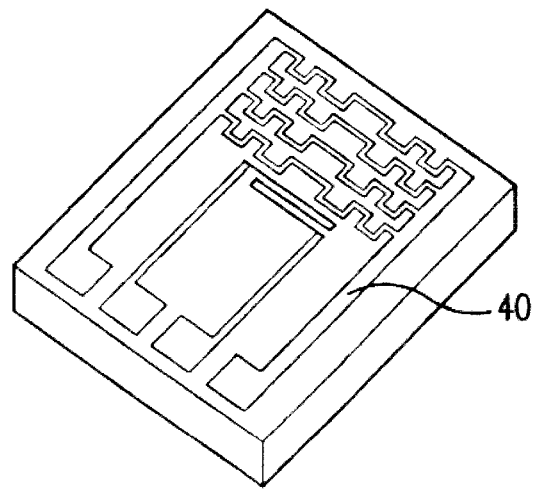

FIG. 5.a shows a top view of a hydrocarbon sensor according to the invention in the form of a coated interdigitated capacitor structure. FIG. 5.b is a sectional view of the interdigitated capacitor structure with a zeolite layer arranged on it, and FIG. 5.c, is a top view of the associated heater structure.

Parallel strip conductors 20 (for example, made of Au) are applied to a substrate 10, such as silica glass, Si or $Al_2O_3$, and are wired such that an arrangement of capacitors is obtained which are electrically switched in parallel. (A single capacitor in each case comprises two adjacent strip conductors.) The gas-permeable sensitive zeolite layer 30 is arranged above and between the strip conductors 20. The layer thickness of the zeolite layer 30 is, for example, on the order of 40 $\mu$m. On the bottom side of the substrate 10, a heater 40 is arranged whose structure consists of individual heater wires, as shown in detail in FIG. 5.c.

EXAMPLE 1

This example illustrates the preparation of the material for the sensitive layer for the selective detection of hydrocarbons in the CO and high-$H_2$ and low-oxygen exhaust gas. Specifically, the following process steps are carried out:

a) Dissolving of Pt(NH_3)4Cl_2*H_2O in distilled water, at a concentration of 0.903 g Pt(NH_3)_4Cl_2*H_2O per 1,000 ml distilled water;

b) producing a suspension by adding 50 g of an NaZSM5 zeolite material per 1,000 ml of to the previously obtained solution;

c) stirring the suspension for 24 hours, followed by filtering, chloride-free washing, and drying at a temperature of 120° C.;

d) gradual heating of the dried powdery material at a constant rate of 4 K/min. to a temperature of approximately 400° C. in an $H_2$-containing atmosphere (for example, 5% per volume of $H_2$ in $N_2$).

EXAMPLE 2

This example illustrates the manner of application of the material for the sensitive layer produced according to Example 1, to an interdigitated capacitor structure. Specifically, the following process steps are carried out:

a) In order to prepare a suspension capable of screen printing from the Pt zeolite material produced according to Example 1, the Pt zeolite powder is mixed at a mass ratio of 1:1 in steps with a suitable screen printing agent, such as WB41 (Zschimmer & Schwarz Co.) in order to achieve a suitable viscosity.

b) The suspension produced according to a) is homogenized by two runs through a rolling mill.

c) The interdigitated capacitor surface is coated with the suspension produced according to a) and b) by means of a screen printing screen (for example, number of meshes 100, mesh width 180 μm, thickness 70 μm/130 μm). The recess windows of the screen printing screen correspond to the dimensions of the interdigitated capacitor surface.

d) The resulting sensor is dried for one hour in air.

e) The sensor is heated with a heating rate of 0.2 K/min. from room temperature to 400° C. in a suitable atmosphere (for example, air), in order to remove the water and the organic constituents from the layer.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for selectively detecting a hydrocarbon in a gas, comprising:

contacting said gas with a gas sensor, said gas sensor comprising a capacitive element and a gas-permeable sensitive dielectric layer in the form of a precious metal-doped zeolite having a regular crystalline structure made of primary pores having a diameter on the order of a gas-kinetic diameter of gas molecules to be detected;

catalytically partially oxidizing said hydrocarbon at a sensor operating temperature;

applying an alternating voltage; and measuring an impedance of the sensor, wherein said gas has an oxygen concentration of less than 10,000 ppm.

2. A method according to claim 1, wherein said zeolite has the precious-metal dotations of a material selected from the group consisting of Pt and Pd.

3. A method according to claim 2, wherein said zeolite is a ZSM5-zeolite.

4. A method according to claim 2, wherein said gas is the exhaust gas of an Otto engine.

5. A method according to claim 1, wherein said zeolite is a ZSM5-zeolite.

6. A method according to claim 5, wherein said ZSM5-zeolite has a Pt-dotation of 3% by weight.

7. A method according to claim 1, wherein said gas is the exhaust gas of an Otto engine.

8. A method according to claim 1, wherein said capacitive element is an interdigitated capacitor.

9. A method according to claim 1, wherein a concentration of said hydrocarbon in said gas is less than 100 ppm.

10. A method according to claim 1, wherein said gas has an oxygen concentration of 0.6%.

11. A method according to claim 1, wherein said gas has an oxygen concentration of 0.2%.

12. A method according to claim 1, wherein said sensor operating temperature is between 300° C. and 500° C.

* * * * *